(12) United States Patent (10) Patent No.: US 7,981,111 B2
Grove et al. (45) Date of Patent: Jul. 19, 2011

(54) METHOD AND APPARATUS FOR THE TREATMENT OF BENIGN PIGMENTED LESIONS

(75) Inventors: Robert E. Grove, Pleasanton, CA (US); Mark V. Weckwerth, Pleasanton, CA (US); Tobin C. Island, Oakland, CA (US)

(73) Assignee: Tria Beauty, Inc., Dublin, CA (US)

( * ) Notice: Subject to any disclaimer, the term of this patent is extended or adjusted under 35 U.S.C. 154(b) by 0 days.

(21) Appl. No.: 10/787,969

(22) Filed: Feb. 25, 2004

(65) Prior Publication Data

US 2004/0167592 A1 Aug. 26, 2004

Related U.S. Application Data

(60) Provisional application No. 60/451,091, filed on Feb. 28, 2003, provisional application No. 60/456,379, filed on Mar. 20, 2003, provisional application No. 60/458,861, filed on Mar. 27, 2003, provisional application No. 60/472,056, filed on May 20, 2003, provisional application No. 60/450,243, filed on Feb. 25, 2003, provisional application No. 60/450,598, filed on Feb. 26, 2003, provisional application No. 60/452,304, filed on Mar. 4, 2003, provisional application No. 60/451,981, filed on Mar. 4, 2003, provisional application No. 60/452,591, filed on Mar. 6, 2003, provisional application No. 60/456,586, filed on Mar. 21, 2003.

(51) Int. Cl.
*A61B 18/08* (2006.01)

(52) U.S. Cl. .......................... 606/27; 607/96

(58) Field of Classification Search .............. 606/27–52; 607/101–105, 96–99
See application file for complete search history.

(56) References Cited

U.S. PATENT DOCUMENTS

| 3,307,533 A | 3/1967 | Liebner |
| 3,538,919 A | 11/1970 | Meyer |
| 3,622,743 A | 11/1971 | Muncheryan |
| 3,693,623 A | 9/1972 | Harte |
| 3,821,510 A | 6/1974 | Muncheryan |
| 3,834,391 A | 9/1974 | Block |
| 4,140,130 A * | 2/1979 | Storm, III ............ 607/154 |
| 4,232,678 A | 11/1980 | Skovajsa |
| 4,240,738 A | 12/1980 | Praamsma |

(Continued)

FOREIGN PATENT DOCUMENTS

CN 2442726 U 8/2001

(Continued)

OTHER PUBLICATIONS

U.S. Appl. No. 10/794,676, filed Mar. 3, 2004, Weckworth et al.

(Continued)

*Primary Examiner* — Michael Peffley
(74) *Attorney, Agent, or Firm* — King & Spalding L.L.P.

(57) ABSTRACT

Disclosed is an apparatus and method which employs an energy source, one or more switches, electronic control circuitry, and a surface that can be placed in contact with a region of a person's skin containing a benign pigmented lesion. Within the apparatus, electrical current is passed through a heating element that is thermally coupled to the surface so that this surface is heated rapidly and then is subsequently cooled rapidly. By judicious choice of the rate of heating, maximum temperatures achieved, and rate of cooling, thermal injury to the skin can be confined primarily to the epidermal region of the skin in contact with the surface.

28 Claims, 3 Drawing Sheets

U.S. PATENT DOCUMENTS

| | | | |
|---|---|---|---|
| 4,354,092 A | 10/1982 | Manabe et al. | |
| 4,388,924 A | 6/1983 | Weissman | |
| 4,423,736 A | 1/1984 | DeWitt et al. | |
| 4,449,528 A * | 5/1984 | Auth et al. | 606/31 |
| 4,551,628 A | 11/1985 | Grossman | |
| 4,573,466 A | 3/1986 | Simada et al. | |
| 4,592,353 A | 6/1986 | Daikuzono | |
| 4,608,978 A | 9/1986 | Rohr | |
| 4,617,926 A | 10/1986 | Sutton | |
| 4,690,141 A | 9/1987 | Castel | |
| 4,733,660 A | 3/1988 | Itzkan | |
| 4,829,262 A | 5/1989 | Furumoto | |
| 4,846,184 A | 7/1989 | Comment et al. | |
| 4,860,744 A * | 8/1989 | Johnson et al. | 606/31 |
| 4,905,690 A | 3/1990 | Ohshiro et al. | |
| 4,930,504 A | 6/1990 | Diamantopoulos et al. | |
| 5,057,104 A | 10/1991 | Chess | |
| 5,059,013 A | 10/1991 | Jain | |
| 5,059,192 A | 10/1991 | Zaias | |
| 5,075,971 A | 12/1991 | McCambridge | |
| 5,107,832 A * | 4/1992 | Guibert et al. | 607/96 |
| 5,109,465 A | 4/1992 | Klopotek | |
| 5,226,907 A | 7/1993 | Tankovich | |
| 5,259,380 A | 11/1993 | Mendes et al. | |
| 5,282,797 A | 2/1994 | Chess | |
| 5,295,052 A | 3/1994 | Chin et al. | |
| 5,344,418 A | 9/1994 | Ghaffari | |
| 5,360,426 A | 11/1994 | Muller et al. | |
| 5,401,270 A | 3/1995 | Muller | |
| 5,405,368 A | 4/1995 | Eckhouse | |
| 5,425,728 A | 6/1995 | Tankovich | |
| 5,431,647 A | 7/1995 | Purcell, Jr. | |
| 5,464,434 A | 11/1995 | Alt | |
| 5,464,436 A | 11/1995 | Smith | |
| 5,473,408 A | 12/1995 | Hoffman et al. | |
| 5,486,172 A | 1/1996 | Chess | |
| 5,519,534 A | 5/1996 | Smith | |
| 5,549,660 A | 8/1996 | Mendes et al. | |
| 5,556,612 A | 9/1996 | Anderson | |
| 5,595,568 A | 1/1997 | Anderson et al. | |
| 5,606,798 A | 3/1997 | Kelman | |
| 5,611,798 A * | 3/1997 | Eggers | 606/31 |
| 5,624,435 A | 4/1997 | Furumoto | |
| 5,628,744 A | 5/1997 | Coleman et al. | |
| 5,630,811 A | 5/1997 | Miller | |
| 5,632,741 A | 5/1997 | Zavislan | |
| 5,643,252 A | 7/1997 | Waner et al. | |
| 5,647,866 A | 7/1997 | Zaias | |
| 5,658,323 A | 8/1997 | Miller | |
| 5,669,916 A | 9/1997 | Anderson | |
| 5,683,380 A | 11/1997 | Eckhouse | |
| 5,700,240 A | 12/1997 | Barwick, Jr. | |
| 5,707,403 A | 1/1998 | Grove | |
| 5,728,090 A | 3/1998 | Martin et al. | |
| 5,735,844 A | 4/1998 | Anderson et al. | |
| 5,743,901 A | 4/1998 | Grove | |
| 5,752,948 A | 5/1998 | Tankovich | |
| 5,752,949 A | 5/1998 | Tankovich | |
| 5,766,214 A | 6/1998 | Mehl, Sr. | |
| 5,769,844 A | 6/1998 | Ghaffari | |
| 5,792,137 A * | 8/1998 | Carr et al. | 606/29 |
| 5,817,089 A | 10/1998 | Tankovich | |
| 5,820,625 A | 10/1998 | Izawa | |
| 5,824,023 A | 10/1998 | Anderson | |
| 5,843,072 A | 12/1998 | Furumoto | |
| 5,846,252 A | 12/1998 | Mehl, Sr. | |
| 5,849,029 A | 12/1998 | Eckhouse | |
| 5,853,407 A | 12/1998 | Miller | |
| 5,868,732 A | 2/1999 | Waldman | |
| 5,871,479 A | 2/1999 | Furumoto | |
| 5,871,480 A | 2/1999 | Tankovich | |
| 5,871,521 A | 2/1999 | Kaneda | |
| 5,879,346 A | 3/1999 | Waldman | |
| 5,885,273 A | 3/1999 | Eckhouse | |
| 5,966,210 A | 10/1999 | Roscow et al. | |
| 5,968,034 A | 10/1999 | Fullmer et al. | |
| 5,989,267 A | 11/1999 | Anderson | |
| 6,015,404 A | 1/2000 | Altshuler | |
| RE36,634 E | 3/2000 | Ghaffari | |
| 6,059,765 A | 5/2000 | Cole | |
| 6,080,146 A | 6/2000 | Altshuler | |
| 6,096,029 A | 8/2000 | O'Donnell, Jr. | |
| 6,106,514 A | 8/2000 | O'Donnell, Jr. | |
| 6,134,475 A * | 10/2000 | Will | 607/98 |
| 6,138,041 A | 10/2000 | Yahia | |
| 6,160,831 A | 12/2000 | Kleinschmidt | |
| 6,183,500 B1 | 2/2001 | Kohler | |
| 6,183,773 B1 | 2/2001 | Anderson | |
| 6,188,495 B1 | 2/2001 | Inoue | |
| 6,197,020 B1 | 3/2001 | O'Donnell, Jr. | |
| 6,208,749 B1 | 3/2001 | Gutkowicz-Krusin et al. | |
| 6,228,074 B1 | 5/2001 | Almeida | |
| 6,251,127 B1 | 6/2001 | Biel | |
| 6,269,818 B1 | 8/2001 | Lui et al. | |
| 6,273,884 B1 | 8/2001 | Altshuler | |
| 6,273,885 B1 | 8/2001 | Koop et al. | |
| 6,277,111 B1 | 8/2001 | Clement | |
| 6,280,438 B1 | 8/2001 | Eckhouse | |
| 6,290,713 B1 | 9/2001 | Russell | |
| 6,322,584 B2 * | 11/2001 | Ingle et al. | 607/96 |
| 6,379,376 B1 | 4/2002 | Lubart | |
| 6,408,212 B1 * | 6/2002 | Neev | 607/100 |
| 6,413,255 B1 * | 7/2002 | Stern | 606/41 |
| 6,436,127 B1 | 8/2002 | Anderson et al. | |
| 6,440,122 B1 | 8/2002 | Shimoji | |
| 6,441,943 B1 | 8/2002 | Roberts | |
| 6,494,900 B1 | 12/2002 | Salansky et al. | |
| 6,508,813 B1 | 1/2003 | Altshuler | |
| 6,511,475 B1 | 1/2003 | Altshuler | |
| 6,514,242 B1 | 2/2003 | Vasily | |
| 6,516,013 B1 | 2/2003 | Patzel | |
| 6,517,532 B1 | 2/2003 | Altshuler | |
| 6,533,775 B1 | 3/2003 | Rizoiu | |
| 6,536,914 B2 | 3/2003 | Hoelen et al. | |
| 6,548,781 B1 | 4/2003 | Brunwinkel | |
| 6,563,853 B2 | 5/2003 | Heist | |
| 6,567,696 B2 * | 5/2003 | Voznesensky et al. | 607/3 |
| 6,600,951 B1 | 7/2003 | Anderson | |
| 6,605,080 B1 | 8/2003 | Altshuler | |
| 6,610,052 B2 | 8/2003 | Furumoto | |
| 6,641,044 B2 | 11/2003 | Plesko | |
| 6,648,904 B2 | 11/2003 | Altshuler | |
| 6,653,618 B2 * | 11/2003 | Zenzie | 250/221 |
| 6,659,999 B1 | 12/2003 | Anderson et al. | |
| 6,660,000 B2 | 12/2003 | Neuberger et al. | |
| 6,663,620 B2 | 12/2003 | Altshuler | |
| 6,663,659 B2 | 12/2003 | McDaniel | |
| 6,666,856 B2 | 12/2003 | Connors et al. | |
| 6,723,090 B2 | 4/2004 | Altshuler et al. | |
| 6,749,624 B2 * | 6/2004 | Knowlton | 607/104 |
| 6,902,563 B2 | 6/2005 | Wilkens et al. | |
| 7,068,910 B2 | 6/2006 | Duine et al. | |
| 7,115,123 B2 * | 10/2006 | Knowlton et al. | 606/41 |
| 7,250,047 B2 * | 7/2007 | Anderson et al. | 606/32 |
| 2001/0023363 A1 | 9/2001 | Harth et al. | |
| 2001/0046131 A1 | 11/2001 | Hoelen et al. | |
| 2002/0005475 A1 | 1/2002 | Zenzie | |
| 2002/0015430 A1 | 2/2002 | Osmanow | |
| 2002/0031160 A1 | 3/2002 | Desor | |
| 2002/0049483 A1 | 4/2002 | Knowlton | |
| 2002/0091377 A1 | 7/2002 | Anderson | |
| 2002/0097587 A1 | 7/2002 | Krietzman | |
| 2002/0128635 A1 | 9/2002 | Altshuler | |
| 2002/0128695 A1 | 9/2002 | Harth et al. | |
| 2002/0151887 A1 | 10/2002 | Stern et al. | |
| 2002/0161357 A1 | 10/2002 | Anderson et al. | |
| 2002/0161418 A1 | 10/2002 | Wilkens et al. | |
| 2002/0173780 A1 | 11/2002 | Altshuler | |
| 2002/0173833 A1 | 11/2002 | Korman et al. | |
| 2002/0183811 A1 | 12/2002 | Irwin | |
| 2003/0004499 A1 | 1/2003 | McDaniel | |
| 2003/0009158 A1 | 1/2003 | Perricone | |
| 2003/0032950 A1 | 2/2003 | Altshuler | |
| 2003/0036751 A1 | 2/2003 | Anderson | |
| 2003/0046825 A1 | 3/2003 | Slingo | |
| 2003/0050561 A1 | 3/2003 | Bazin et al. | |
| 2003/0055413 A1 | 3/2003 | Altshuler | |

| | | |
|---|---|---|
| 2003/0055414 A1 | 3/2003 | Altshuler |
| 2003/0065314 A1 | 4/2003 | Altshuler |
| 2003/0080755 A1 | 5/2003 | Kobayashi |
| 2003/0094714 A1 | 5/2003 | Buazza et al. |
| 2003/0105069 A1 | 6/2003 | Robinson et al. |
| 2003/0133292 A1 | 7/2003 | Mueller et al. |
| 2003/0138249 A1 | 7/2003 | Merola et al. |
| 2003/0146122 A1 | 8/2003 | Westfield et al. |
| 2003/0169400 A1 | 9/2003 | Buazza et al. |
| 2003/0177657 A1 | 9/2003 | Andis |
| 2003/0195494 A1 | 10/2003 | Altshuler et al. |
| 2003/0199859 A1 | 10/2003 | Altshuler et al. |
| 2003/0216795 A1 | 11/2003 | Harth et al. |
| 2003/0233138 A1 | 12/2003 | Spooner |
| 2004/0006328 A1 | 1/2004 | Anderson |
| 2004/0010298 A1 | 1/2004 | Altshuler |
| 2004/0010299 A1 | 1/2004 | Tolkoff |
| 2004/0034319 A1 | 2/2004 | Anderson et al. |
| 2004/0034341 A1 | 2/2004 | Altshuler et al. |
| 2004/0036975 A1 | 2/2004 | Slatkine |
| 2004/0073079 A1 | 4/2004 | Altshuler et al. |
| 2004/0093042 A1 | 5/2004 | Altshuler et al. |
| 2004/0120151 A1 | 6/2004 | Ostler et al. |
| 2004/0122492 A1 | 6/2004 | Harth et al. |
| 2004/0167499 A1 | 8/2004 | Grove |
| 2004/0167500 A1 | 8/2004 | Weckwerth et al. |
| 2004/0167501 A1 | 8/2004 | Island et al. |
| 2004/0167502 A1 | 8/2004 | Weckwerth et al. |
| 2004/0176754 A1 | 9/2004 | Island et al. |
| 2004/0176823 A1 | 9/2004 | Island et al. |
| 2004/0225339 A1 | 11/2004 | Yaroslavsky et al. |
| 2005/0276072 A1 | 12/2005 | Hayashi et al. |
| 2006/0142750 A1* | 6/2006 | Da Silva et al. ............... 606/27 |
| 2006/0206103 A1 | 9/2006 | Altshuler et al. |
| 2007/0129711 A1 | 6/2007 | Altshuler et al. |

FOREIGN PATENT DOCUMENTS

| | | |
|---|---|---|
| DE | 196 29 978 A1 | 1/1998 |
| EP | 0 933 096 A2 | 8/1999 |
| EP | 1 116 476 A2 | 7/2001 |
| EP | 1 168 535 A1 | 1/2002 |
| EP | 0 761 257 A2 | 3/2003 |
| FR | 2 665 366 | 2/1992 |
| JP | 11-244295 | 9/1999 |
| JP | 2000-300683 | 10/2000 |
| WO | WO 00-02491 | 1/2000 |
| WO | WO 02-094116 A1 | 11/2002 |
| WO | 03/001984 A2 | 1/2003 |
| WO | WO 03-017824 A2 | 3/2003 |
| WO | WO 03-049633 A1 | 6/2003 |

OTHER PUBLICATIONS

Sliney, David, et al., "Safety With Lasers and Other Optical Sources, A Comprehensive Handbook", Plenum Press (1985), pp. 223-224, 477-480.
Hode, L., "Are Lasers More Dangerous Than IPL Instruments?", Lasers In Surgery and Medicine, Supplement, 15, 2003, p. 6; and poster presentation at corresponding conference.
2002 Skin & Aging, Supplement to Nov. 2002, "Harnessing Light to Treat Stretch Marks and Other Hypopigmented Scars", pp. 1-4.
Predicate Devices: LightSheer Diode Laser System by Star Medical/Coherent Star in 1997, K973324, K982940, K001746.
International Standard IEC 60825.1, Safety of Laser Products—Part 1: Equipment Classification, Requirements and User's Guide, Edition 1.2, Aug. 2001, p. 11; p. 40, note 2, Sub-note D; p. 52; p. 79.
Micro Touch Trimmer website, www.assenontvwork.com/vcc/ideavillage/microtouch/104917, printed Dec. 4, 2003, 21 pages.
Morys et al., "The Accurate Measurements Of Biologically Effective Ultraviolet Radiation", Jul. 1993, 10 pages.
UV Index definition, Canadian Environmental Web page, Jun. 1, 1996, See entire document, 3 pages.
Guideline for Limits of Exposure to Ultraviolet Radiation of Wavelengths between 180 nm and 400 nm, Health Physics, vol. 49, No. 2, Aug. 1985, pp. 331-340.
Kjeldstad B, et al., "Porphyrin photosensitization of bacteria," Adv Exp Med Biol. 1985;193:155-9. PMID: 4096295 [PubMed—indexed for MEDLINE], 6 pages.

Arakane K, et al., "Singlet oxygen (1 delta g) generation from coproporphyrin in Propionibacterium acnes on irradiation," Biochem Biophys Res Commun. Jun. 25, 1996;223(3):578-82. PMID: 8687438 [PubMed—indexed for MEDLINE], 5 pgs.
Ashkenazi H, et al., "Eradication of Propionibacterium acnes by its endogenic porphyrins after illumination with high intensity blue light." FEMS Immunol Med Microbiol. Jan. 21, 2003;35(1):17-24. PMID: 12589953 [PubMed—indexed for MEDLINE], 8 pgs.
Cornelius CE 3rd, et al., "Red fluorescence of comedones: production of porphyrins by Corynebacterium acnes," J Invest Dermatol. Oct. 1967;49(4):368-70. PMID: 4228644 [PubMed—indexed for MEDLINE], 3 pgs.
Fanta D, et al., "Porphyrinsynthesis of Propionibacterium acnes in acne and seborrhea (author's transl)," Arch Dermatol Res. Apr. 7, 1978;261(2):175-9. German. PMID: 148872 [PubMed—indexed for MEDLINE], 5 pgs.
Formanek I, et al., "[Porphyrinsynthesis by propionibacterium acnes (author's transl]," Arch Dermatol Res. Aug. 22, 1977;259(2):169-76. German. PMID: 334087 [PubMed—indexed for MEDLINE], 8 pgs.
Kawada A, et al., "Acne phototherapy with a high-intensity, enhanced, narrow-band, blue light source: an open study and in vitro investigation," J Dermatol Sci. Nov. 2002;30(2):129-35. PMID: 12413768 [PubMed—indexed for MEDLINE], 7 pgs.
Kjeldstad B, et al., "An action spectrum for blue and near ultraviolet inactivation of Propionibacterium acnes; with emphasis on a possible porphyrin photosensitization," Photochem Photobiol. Jan. 1986;43(1):67-70. PMID: 3952162 [PubMed—indexed for MEDLINE], 4 pgs.
Kjeldstad B, et al., "Influence of pH on porphyrin production in Propionibacterium acnes," Arch Dermatol Res. 1984;276(6):396-400. PMID: 6517611 [PubMed—indexed for MEDLINE], 5 pgs.
Lee WL, et al., "Comparative studies of porphyrin production in Propionibacterium acnes and Propionibacterium granulosum," J Bacteriol. Feb. 1978;133(2):811-5. PMID: 637914 [PubMed—indexed for MEDLINE], 5 pgs.
McGinley KJ et al., "Facial follicular porphyrin fluorescence: correlation with age and density of Propionibacterium acnes," Br J Dermatol. Apr. 1980;102(4):437-41. PMID: 7387886 [PubMed—indexed for MEDLINE], 5 pgs.
Meffert H, et al., "Therapy of acne with visible light. Decreased irradiation time by using a blue-light high-energy lamp [transl.]," Dermatol Monatsschr. 1990;176(10):597-603. German. PMID: 2150382 [PubMed—indexed for MEDLINE], 7 pgs.
Meffert H, et al., "Phototherapy of acne vulgaris with the "TuR" UV 10 body section irradiation unit [transl.]," Dermatol Monatsschr. 1986;172(1):9-13. German. PMID: 2938991 [PubMed—indexed for MEDLINE], 6 pgs.
Meffert H, et al., "Phototherapy of acne vulgaris with the UVA irradiation instrument TBG 400[transl.]," Dermatol Monatsschr. 1986;172(2):105-6. German. PMID: 2937663 [PubMed—indexed for MEDLINE], 2 pgs.
Meffert H, et al., "Treatment of acne vulgaris with visible light," Dermatol Monatsschr. 1987;173(11):678-9. German. PMID: 2963772 [PubMed—indexed for MEDLINE], 2 pgs.
Kjeldstad B, et al., "Near-UV-induced radicals in Propionibacterium acnes, studied by electron spin resonance spectrometry at 77 K.," J Photochem Photobiol B. May 1991; 9(2):181-7. PMID: 1650821 [PubMed—indexed for MEDLINE], 7 pgs.
Johnsson A, et al., "Fluorescence from pilosebaceous follicles," Arch Dermatol Res. 1987;279(3):190-3. PMID: 3592747 [PubMed—indexed for Medline], 4 pgs.
Melo TB, et al., "Photodestruction of Propionibacterium acnes porphyrins," Z Naturforsch [C]. Jan.-Feb. 1985;40(1- 2):125-8. PMID: 3993179 [PubMed—indexed for MEDLINE], 4 pgs.
Melo TB, et al., "In vivo porphyrin fluorescence for Propionibacterium acnes. A characterization of the fluorescing pigments," Dermatologica. Mar. 1982;164(3):167-74. PMID: 7084539 [PubMed—indexed for MEDLINE], 8 pgs.
Mills OH, et al., "Ultraviolet phototherapy and photochemotherapy of acne vulgaris," Arch Dermatol. Feb. 1978;114(2):221-3. PMID: 147054 [PubMed—indexed for MEDLINE], 3 pgs.

Papageorgiou P, et al., "Phototherapy with blue (415 nm) and red (660 nm) light in the treatment of acne vulgaris," Br J Dermatol. May 2000;142(5):973-8. PMID: 10809858 [PubMed—indexed for MEDLINE], 6 pgs.

Romiti R, et al., "High-performance liquid chromatography analysis of porphyrins in Propionibacterium acnes," Arch Dermatol Res. Jun. 2000;292(6):320-2. PMID: 10929774 [PubMed—indexed for MEDLINE], 3 pgs.

Sigurdsson V, et al., "Phototherapy of acne vulgaris with visible light," Dermatology. 1997;194(3):256-60. PMID: 9187844 [PubMeD—indexed for MEDLINE], 5 pgs.

Webster, GF, "Inflammation in acne vulgaris," J Am Acad Dermatol. Aug. 1995;33(2 Pt 1):247-53. Review. PMID: 7622652 [PubMed—indexed for MEDLINE], 7pgs.

Fanta D, et al., "Porphyrin synthesis by propionibacteria in dependence of external factors." Arch Dermatol Res (1981) 271:127-133, 7 pgs.

Leyden J, "Therapy for acne vulgaris," New England Journal of Medicine, Apr. 17, 1997, Review Article, 6 pgs.

Leung, S, "The Porphyrin Page" website at http:--www.washbum.edu-cas-chemistry-sleung-porphyrin-porphyrin_page.html, Created Apr. 16, 1996, Last Modified Nov. 11, 2002, printed Jun. 22, 2004, 7 pgs.

Brunsting, L.A. et al., "The Color of the Skin as Analyzed by Spectrophotometric Methods: III. The Role of Superficial Blood", The Journal of Clinical Investigation, 1929, vol. 7, pp. 593-613.

Brunsting, L. A. et al., "The Color of the Skin as Analyzed by Spectrophotometric Methods: II. The Role of Pigmentation", The Journal of Clinical Investigation, 1929, vol. 7, pp. 574-592.

Angelopoulou et al., "The Reflectance Spectrum of Human Skin", Technical Report, Department of Computer and Information Science, 1999, pp. 1-14.

European Office Action, European application No. 04 714 604.8, 5 pages, Nov. 16, 2010.

European Office Action, European application No. 04 712 910.1, 6 pages, Nov. 16, 2010.

Supplemental European Search Report, European application No. 04 712 922. 6, 3 pages, Jul. 12, 2010.

Supplemental European Search Report, European application No. 04 712 911. 9, 3 pages, Jun. 12, 2010.

* cited by examiner

METHOD AND APPARATUS FOR THE TREATMENT OF BENIGN PIGMENTED LESIONS

PRIORITY

This application claims the benefit of priority under 35 U.S.C. §119(e) to U.S. provisional patent applications No. 60/451,091, filed Feb. 28, 2003; 60/456,379, filed Mar. 20, 2003; 60/458,861, filed Mar. 27, 2003; 60/472,056, filed May 20, 2003; 60/450,243, filed Feb. 25, 2003; 60/450,598, filed Feb. 26, 2003; 60/452,304, filed Mar. 4, 2003; 60/451,981, filed Mar. 4, 2003; 60/452,591, filed Mar. 6, 2003; and 60/456,586, filed Mar. 21, 2003.

FIELD OF THE INVENTION

The present invention relates generally to dermatologic treatment methods and apparatus, and in particular to an apparatus and method for treatment of benign pigmented lesions.

BACKGROUND ART

Description of the Related Art

Benign pigmented lesions are extremely common in both men and women, with estimates as high as 30-40% of adults. The lesions appear brown in color due to an excess of melanin in a localized area compared to the surrounding, lighter-colored skin. Those lesions in which the excess melanin is primarily or exclusively confined to the upper layer of skin (the epidermis) are often referred to medically as lentigines, or commonly as age spots, liver spots or freckles.

Despite their harmless nature, these lesions are often viewed as cosmetically undesirable, especially by women. As a result many treatment modalities have been employed by dermatologists for generations. Conventional treatment methods include topical creams such as hydroquinone; chemical or mechanical peels such as glycolic acid or dermabrasion; and various forms of cryotherapy using liquid nitrogen, dry ice or a sprayed refrigerant such as Freon.

However, all of these methods have significant drawbacks. Topical creams having any degree of effectiveness require prescriptions, cause only modest lightening, and necessitate sun avoidance to prevent subsequent re-darkening of the lesions. Chemical or mechanical destruction of the epidermis is problematic because of the risk of unwanted damage to the underlying dermis, which can result in permanent scarring. Similarly, crude thermal injury to the epidermis (typically by very cold substances, and thus termed cryotherapy) also runs the risk of dermal injury due to the difficulty in controlling the depth of cold-induced cell death. On the other hand, overly conservative treatment to avoid scarring inevitably results in the absence of any therapeutic benefit.

Because of its simplicity and low cost, cryotherapy is the most common conventional treatment method. Regions of the epidermis containing excessive pigmentation are intentionally damaged, and the body regenerates new epidermal tissue with normal levels of pigment, matching the skin surrounding the lesion. Adjacent regions of epidermis which are normally pigmented, but which are inadvertently also damaged by the cryotherapy, also rapidly heal with normal pigmentation.

The superficial nature of the excess pigmentation, and the ability of the body to regenerate the epidermis without scarring, suggest that even simpler methods might be employed to treat these lesions. For example, one might imagine that a simple heated rod, pressed against the skin, could effect the desired thermal damage. However, in practice such a device either causes insufficient heating to effect pigmentation change, or creates unwanted deeper (dermal) injury, resulting in a blister or scar. In addition, it is quite painful.

More recently, lasers and intense pulsed light (IPL) sources have gained acceptance among dermatologists for treatment of benign pigmented lesions. The absorption of light by melanin causes localized heating and thus the desired thermal injury to the melanized epidermal layer. Because the lesion (by definition) contains a higher concentration of melanin than the surrounding skin, heat is created preferentially in the area of the lesion as opposed to the adjacent normally-pigmented skin. Through careful choice of wavelength, fluence and pulse duration, considerable lightening or occasionally complete clearing of these lesions can be achieved after three to five treatments.

Light-based treatments of benign pigmented lesions have the dual advantages of light-absorption-based (and thus targeted) heating, as well as good control of the amount and time duration of energy deposition. Thus the risks of scarring or under-treatment are greatly reduced, and these methods have largely replaced cryotherapy among physicians having access to a laser or IPL. However, major disadvantages remain. First, the devices cost tens of thousands of dollars, and can be used only by medical professionals. Secondly, multiple treatments are almost always required. In contrast, when cryotherapy is done such that thermal damage is aggressive enough to cause cell death and yet is limited to the epidermis (a difficult task), the lesion often clears in a single treatment.

The above results suggest that, if the desired thermal injury can be created by some much simpler and less expensive means than laser or IPL, and at the same time confined primarily to the epidermis, a safe, therapeutic outcome would result using a device of much lower cost. In addition, if such a device were designed so that the total energy delivered to the skin is limited, the device could in principle be sufficiently safe for home use. In this way the cost and inconvenience of doctor's appointments could be totally avoided.

Current State of the Art

In an attempt to achieve controlled heating of the epidermis, at least one product has been developed that utilizes a diode laser to heat a metal cap placed against the skin (Y-Beam Technologies, Lake Forest, Calif.). This approach enables rapid, controlled heating of a surface in contact with the skin, but provides no means for subsequent rapid cooling of this surface. Thus the same inherent difficulties described above limit the utility of this device in effecting controlled thermal injury to the epidermis.

In U.S. Pat. No. 6,660,000 Neuberger et al describe a device utilizing light energy to treat a variety of dermatologic conditions. Fuller et al (U.S. Pat. No. 5,968,034) discloses a pulsed, high-energy filament lamp for similar applications. A multitude of laser sources for treatment of biologic targets is described in U.S. Pat. No. 6,610,052 to Furumoto, and use of diode lasers for dermatologic applications including pigmented lesions is disclosed in U.S. Pat. No. 5,658,323 to Miller. However, in all of the above inventions, treatment of the lesion results from the application of light energy, which induces thermal injury to the skin. None discloses the application of heat energy directly, followed by rapid cooling of the skin.

SUMMARY OF THE INVENTION

Therefore, in view of and in accordance with the above, an apparatus and method is provided for the treatment of a benign pigmented lesion. The apparatus includes an energy source, one or more switches, and electronic control circuitry. The apparatus has a surface that is placed in contact with a region of a person's skin containing a benign pigmented lesion. Within the apparatus is a heating element that is heated by passing electrical current through the element and that is thermally coupled to the surface. When current is passed through the heating element, this surface is heated rapidly and then is subsequently cooled rapidly. By judicious choice of the rate of heating, maximum temperatures achieved, and rate of cooling, the thermal injury can be confined primarily to the epidermal region of the skin in contact with the surface. Thermal injury, primarily within the epidermis containing the benign pigmented lesion, stimulates a healing process and subsequent normal re-pigmentation of the skin.

This rapid heating and subsequent rapid cooling is termed a thermal pulse. Activation of the heating element may be achieved by having a user of the apparatus depress a button on the housing. Alternatively, in a preferred embodiment, activation of the heating element is achieved by activation of a contact sensor located near the surface of the apparatus in contact with the skin. This contact sensor may be a type of membrane switch such that, when the apparatus is pressed against the skin, the membrane switch closes, initiating the thermal pulse.

In an alternative embodiment, the surface is cooled to a temperature below an average temperature of the skin prior to contact with the skin surface. For example, the surface may be cooled to a temperature of 5-25 degrees Celsius. Temperatures above 25 degrees C. provide little cooling effect, and temperatures near or below 0 degrees C. create problems with excessive condensation and/or ice on the surface. The pre-cooling of the surface, and especially the rapid cooling of the surface following heating further serve to reduce the discomfort associated with the use of the device.

In yet another preferred embodiment, the apparatus may be hand-held and self-contained, thereby eliminating the need to use the device near an electrical outlet. This cordless device utilizes one or more batteries for its source of electrical power. To dispose of waste heat, and for effecting pre-cooling if desired, one or more heat-removal elements are included within the hand-held apparatus. The one or more heat-removal elements may be a conventional finned heat sink and fan, or may incorporate a more type of thermal battery described in more detail below.

In accordance with the present invention a method of treatment of a benign pigmented lesion utilizes an apparatus which includes an energy source, a surface configured for contact with the benign pigmented lesion and capable of being rapidly heated and rapidly cooled, an ohmic heating element, and a heat removal element. The method includes coupling the ohmic heating element between the heat removal element and the surface in a manner so that heat is transferred more quickly to the surface than to the heat removal element, applying a designated amount of power to the ohmic heating element from the energy source to produce a rapid heating of the surface for a designated period of time, removing power from the ohmic heating element following the designated period of time so that heat can flow between the surface and the heat removal element to provide a rapid cooling of the surface, whereby, during operation of the apparatus, thermal injury to the region of skin in contact with the surface is limited primarily to an epidermal layer.

In accordance with a method of the present invention, the apparatus can further include one or more switches, so that a step can involve controlling the application of power to the ohmic heating element with the one or more switches. Where one or more of the switches is a contact sensor positioned near the surface to detect substantial contact between the surface and skin, a further embodiment of the method of the present invention can involve the step of inhibiting the application of power to the ohmic heating element unless the substantial contact is detected by the contact sensor. In another embodiment the detection of substantial contact initiates the application of power to the ohmic heating element.

In another embodiment of the above method, power is applied in a manner so that the rapid heating of the surface heats the lesion to a temperature of at least 60 degrees Celsius in less than 200 milliseconds, and the subsequent rapid cooling of the surface cools the lesion to a temperature of less than 50 degrees Celsius in less than 500 milliseconds.

Further steps in a method of the present invention involve cooling the surface below an average temperature of the skin, and placing the surface in contact with the skin prior to applying power to the ohmic heating element.

It is therefore an object of the present invention to provide an apparatus and method for treatment of benign pigmented lesions which employs a thermal pulse applied to the lesion through contact with a surface.

It is another object of the present invention to provide an apparatus and method for treatment of benign pigmented lesions which employs the rapid heating and subsequent rapid cooling of a surface which is configured for contact with a region of skin having a benign pigmented lesion, in which the surface is capable of being rapidly heated from an ohmic heating element and can rapidly transfer such heat to the lesion, and in which the surface is capable of being rapidly cooled, once the ohmic heating-element has been turned off, through a thermal coupling to a heat removal element.

It is a further object of the present invention to provide a method and apparatus for treatment of benign pigmented lesions in a region of skin in which a thermal pulse is supplied to the lesion through contact with a surface that is rapidly heated through an ohmic heating element and subsequently rapidly cooled, and in which a contact sensor is employed to inhibit the activation of the ohmic heating element when a contact sensor indicates the absence of contact between the surface and the region of skin.

These and other objectives, features and advantages of the present invention will be more readily understood upon consideration of the following detailed description of certain preferred embodiments, and accompanying drawings.

INCORPORATION BY REFERENCE

What follows is a list of citations corresponding to references which are, in addition to those references cited above and below, and including that which is described as background and the invention summary, hereby incorporated by reference into the detailed description of the preferred embodiments below, as disclosing alternative embodiments of elements or features of the preferred embodiments that may not otherwise be set forth in detail below. A single one or a combination of two or more of these references may be consulted to obtain a variation of the elements or features of preferred embodiments described in the detailed description below. Further patent, patent application and non-patent references are cited in the written description and are also incorporated by reference into the preferred embodiment with the same effect as just described with respect to the following references:

U.S. Pat. Nos. 5,658,323; 5,968,034; 6,610,052; 6,660,000; U.S. provisional patent applications No. 60/451,091, filed Feb. 28, 2003; 60/456,379, filed Mar. 20, 2003; 60/458,861, filed Mar. 27, 2003; 60/472,056, filed May 20, 2003; 60/450,243, filed Feb. 25, 2003; 60/450,598, filed Feb. 26, 2003; 60/452,304, filed Mar. 4, 2003; 60/451,981, filed Mar. 4, 2003; 60/452,591, filed Mar. 6, 2003; and 60/456,586, filed Mar. 21, 2003, all of which are assigned to the assignee of the subject application (collectively, the "Cross-Referenced Provisional Applications"); and U.S. non-provisional patent application Ser. No. 10/783,880, filed Feb. 19, 2004, entitled "Self-Contained Eye-Safe Hair-Regrowth-Inhibition Apparatus And Method," naming as inventors Tobin C. Island, Robert E. Grove, and Mark V. Weckwerth; Ser. No. 10/783,603, filed Feb. 19, 2004, entitled "Eye-Safe Dermatologic Treatment Apparatus And Method," naming as inventors: Robert E. Grove, Mark V. Weckwerth, Tobin C. Island; and Ser. No. 10/783,607, filed Feb. 19, 2004, entitled "Self-Contained, Diode-Laser-Based Dermatologic Treatment Apparatus And Method," naming as inventors: Mark V. Weckwerth, Tobin C. Island, Robert E. Grove, all of which are assigned to the assignee of the subject application (collectively "the Cross-Referenced Non-Provisional Applications").

DETAILED DESCRIPTION OF THE PREFERRED EMBODIMENTS

Figure 1:
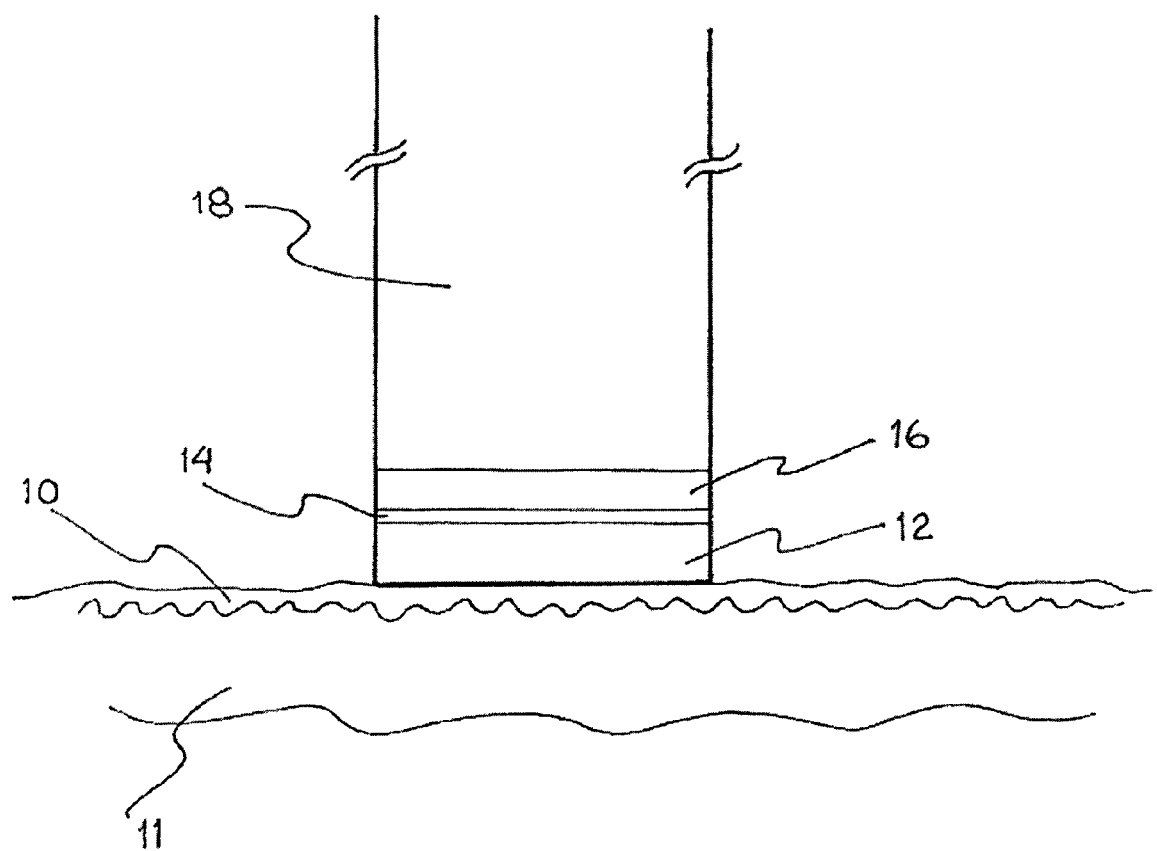
FIG. 1 schematically illustrates an apparatus for the treatment of benign pigmented lesions in accordance with the present invention.

In the preferred embodiment of the device (FIG. 1), the surface contacting the epidermis 10 is a sheet 12 of material having sufficiently high thermal conductivity and sufficiently low thermal mass as to allow heating and cooling in milliseconds; such heating being achieved by either placement of a heating element 14 (or elements) on said sheet, or by designing sheet 12 to serve as its own heating element by virtue of its own electrical resistance. This type of heating is termed ohmic heating. (Suitable materials for sheet 12 and its means of heating 14 are discussed in more detail below.)

Sheet 12 and its means of heating 14 are in turn backed by a sheet of material 16 which serves as a thermal insulator (on a time scale of milliseconds) but which is a thermal conductor on longer time scales (on the order of seconds). The presence of this thermally insulating layer temporarily isolates sheet 12 from the cooled heat-removal element 18, allowing sheet 12 to be rapidly heated. Insulating sheet 16 is in turn backed by a large heat-removal element 18, as for example a block of copper or aluminum that has been cooled to a temperature below that of the skin surface.

The device in a preferred embodiment is first activated for a period of time, perhaps tens of seconds, during which time the heat-removal element 18 is cooled below the skin surface temperature, and during which time sheets 16 and 12 are also cooled. The device is then placed against the skin surface (at a location containing all or a portion of a benign pigmented lesion) and pressed against the skin for a period of seconds to pre-cool both the contacted epidermis 10 and some fraction of the underlying dermis 11. Sheet 12 is then rapidly heated (rising in temperature to near 100 degrees Celsius in a time period of the order of milliseconds) by passing electrical current through a heating element or heating elements 14 in contact with the sheet or though the sheet itself.

The rapid heating of the sheet 12 in contact with the skin causes heat to propagate through the epidermis 10, causing the desired thermal damage. However, because the portion of the dermis 11 adjacent to the epidermis has been pre-cooled, and because the sheet 12 in contact with the skin is backed by the cooled heat-removal element 18, the heated epidermis rapidly cools (after the electrical current is turned off) by thermal conduction both downward into the dermis and upward into the cooled thermal mass of the device. Thus the device design allows for a thermal pulse that is analogous to that induced by a laser or IPL, but in a much simpler and lower cost manner.

The heating of sheet 12 can be precisely controlled by virtue of the electrical energy deposited, and the cooling of sheet 12 can be equally controlled by the design (e.g., thickness and choice of material) of the thermally insulating sheet 16, of the heat-removal element 18, and of sheet 12 itself. Thus the drawbacks of other more elaborate thermal approaches, like a laser-heated metal cap, or simple thermal approaches such as cryotherapy, are avoided. As described above, these drawbacks include over-treatment resulting in scarring, or under-treatment resulting in lack of efficacy.

The energy requirements to cool the heat-removal element 18 below skin temperature and to heat the sheet 12 in contact with the skin are small; thus the entire device can be battery-powered in its preferred embodiment. The heat-removal element 18 itself may be a "thermal battery" containing, for example, a block of copper having a high heat capacity. In this design, the thermal battery may be "charged" by placing the entire apparatus in a refrigerator. Alternatively, the thermal battery may contain a material having a melting point somewhat below the skin temperature; the resulting phase change upon heat input clamps the temperature of the material at the melting point until sufficient heat is absorbed to overcome the heat of fusion of the material. Alternatively, the heat-removal element 18 could be a thermo-electric module. Yet another type of heat-removal element 18 comprises a conventional finned heatsink and fan for discharging waste heat into the air. Further discussion and details about heat removal elements, thermal batteries, and heatsinks suitable for use in the present invention can be found in the above mentioned Cross-Referenced Non-Provisional Applications.

A sensor near the tip of the device may also be incorporated to ensure that the device has been in contact with the skin for a sufficient cooling period, prior to activation of the heating element. This sensor can be a simple contact sensor such as a micro-switch or membrane switch that is closed when the tip is pressed against a firm surface such as the skin. These types of switches are well known to those skilled in the art, and are widely used in a variety of products, such as cell phones.

In an alternative embodiment of the device, the device is not pre-cooled, and the desired epidermal damage is achieved by virtue of the rapid heating and rapid cooling described herein, without prior cooling of the skin below its average temperature.

In addition to its small overall size and battery-powered operation, the limited heating and rapid cooling of the surface of the device in contact with the skin makes the device safe for use by individuals with no medical training. Thus the invention permits, for the first time, effective and safe home treatment of benign pigmented lesions.

Materials and Methods for Construction of the Device

Sheet 12 is preferably a disc or rectangle of the order of one square centimeter in area, and is constructed so that it can be heated rapidly (on the order of milliseconds) by an electrical current. To construct a prototype of the device, a sheet of silicon (University Wafer, South Boston, Mass.) was coated in a vacuum chamber with a thin (~1000 Angstroms) layer of nickel. A serpentine pattern was drawn on the nickel with a pen containing an etch-resistant ink. The silicon sheet was then placed in an acid bath to remove the unprotected regions of the nickel coating, leaving a conductive path of nickel to serve as the heating element 14. This method of creating a conductive path (in this case, with some resistance) is similar to that used for creating printed circuit boards, and is well known to those familiar with the art. Alternatively, a conductive path could be created in the silicon by ion implantation, or by bonding of conventional heating elements to its surface. The insulating layer 16 utilized in the prototype was a piece of transparent tape, although there are many other possible choices, such as glass or mica.

To provide electrical current to the heating element 14, a battery is the preferred embodiment (to allow portability of the device) although a standard electrical cord and outlet could alternatively be used. Further discussion and details about battery packs, and battery powered configurations, and circuitry for controlling the above components, suitable for use in the present invention can be found in the above mentioned Cross-Referenced Non-Provisional Applications.

Figure 2:
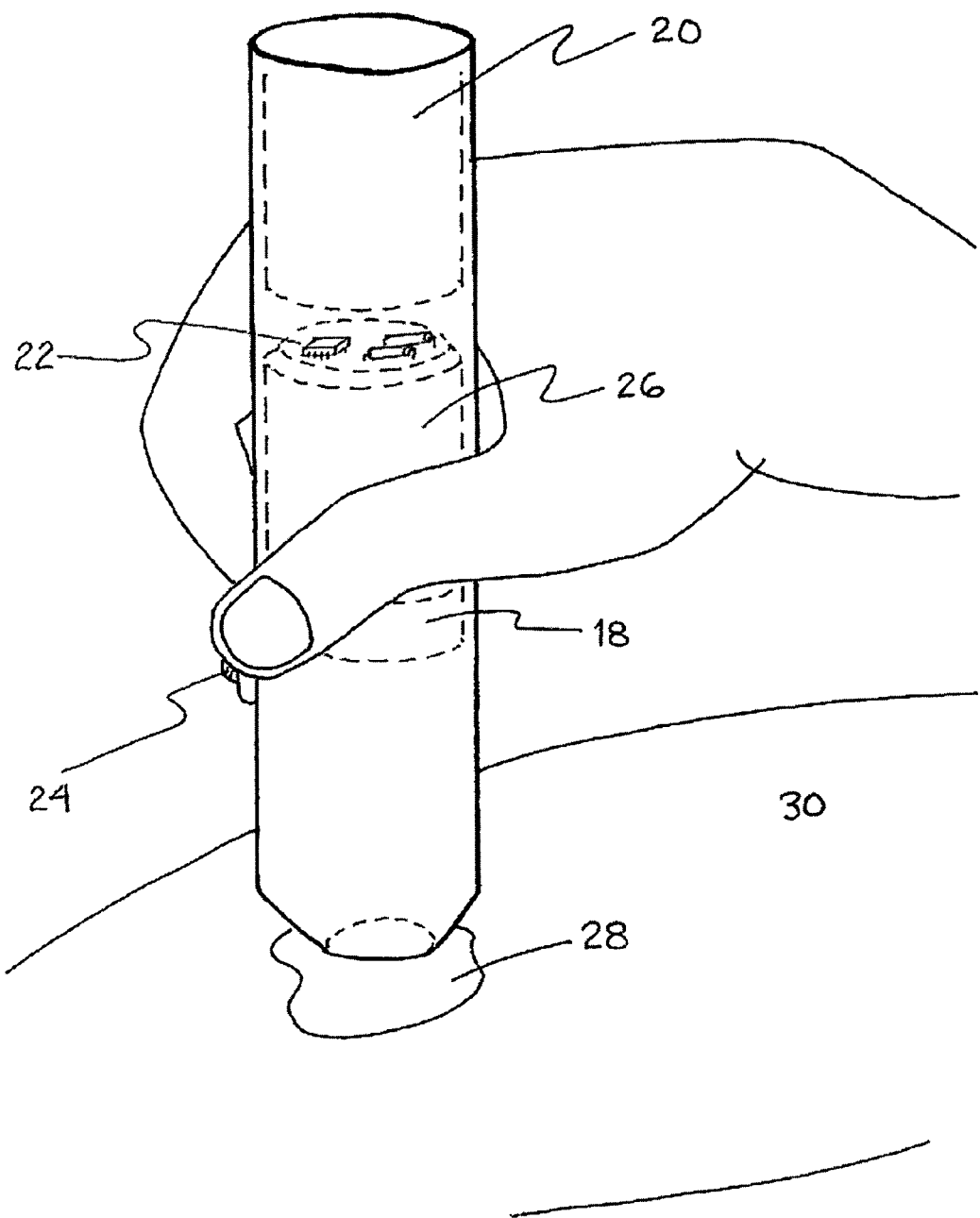
FIG. 2 schematically illustrates a perspective view of a hand-held, self-contained apparatus for causing heat-induced thermal injury to a region of a person's skin in accordance with the present invention.

FIG. 2 shows one possible embodiment of the device, in a form that is both handheld and battery-powered. Output from the battery 20 passes through a standard capacitor-charging circuit 22, when switch 24 is depressed. FIG. 2 also shows a possible location of the heat-removal element 18, and a possible location of a chamber containing a phase-change material 26 to maintain the cooled temperature of the heat-removal element. The device is placed against a benign pigmented lesion 28 located on the patient 30.

Figure 3:
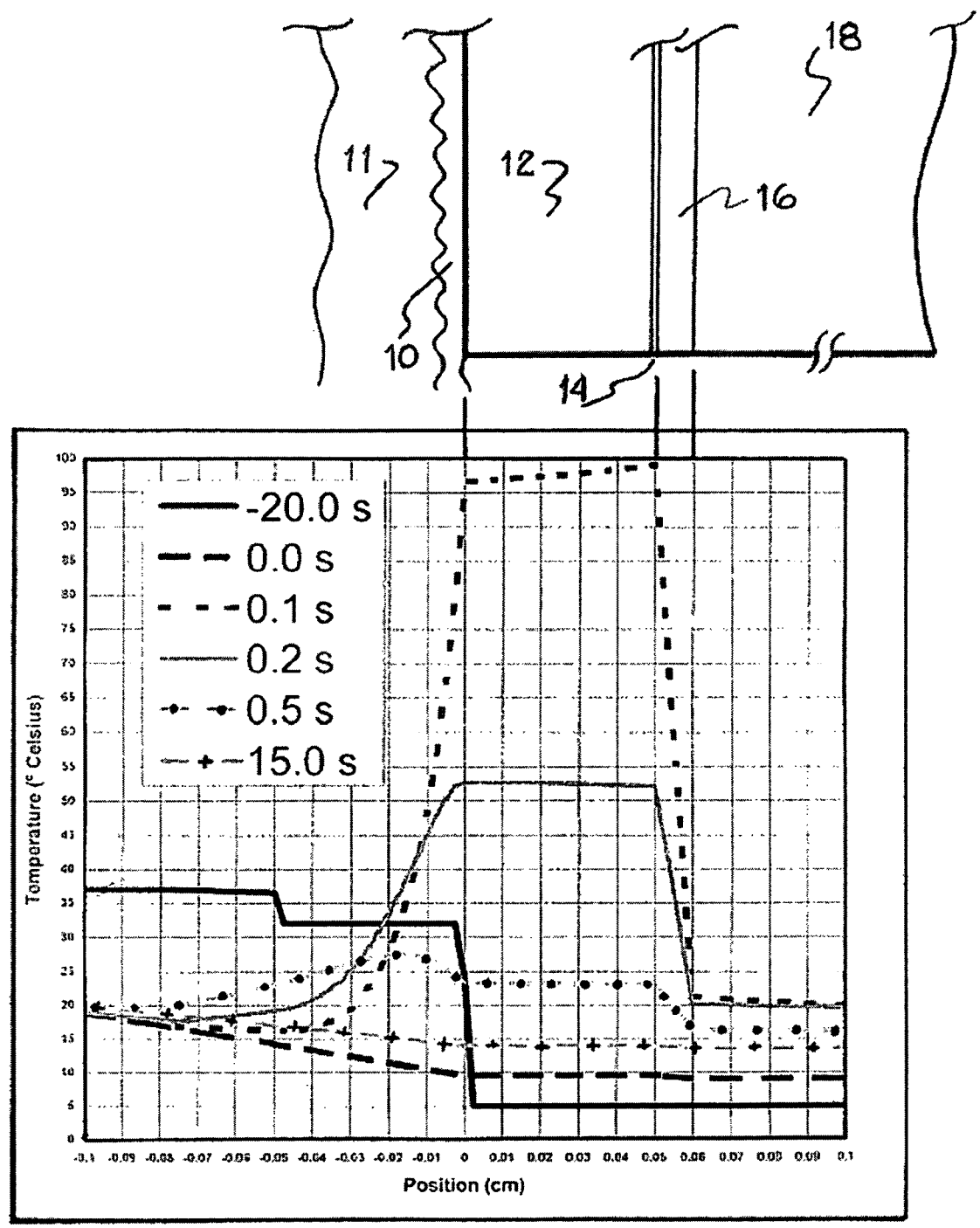
FIG. 3 displays a graph of temperatures of various elements of the apparatus and of the skin as a function of position, and at a variety of different times. For purposes of clarification, a schematic drawing of a portion of the apparatus is drawn in the proper scale and with the proper alignment with respect to the graph, to help correlate the position coordinates on the abscissa of the graph with the physical elements of the apparatus.

To establish and confirm the proper design of the device, a finite-difference heat transfer model was developed, and many cases run on a personal computer to determine the regions of heating and cooling, and the corresponding temperatures and time scales. An example of these simulations is contained in FIG. 3, which shows the temperatures of the skin and of the device as a function of distance, for several different times. In the figure, note that the device has been oriented to align with the graph, with the skin surface located at 0.0 cm. For the computer simulation, the following materials and values are used: silicon is utilized as sheet 12 having a thickness of 0.5 mm, backed by a nickel trace 14 having an electrical resistance of approximately 100 ohms and into which an electrical energy of 20.0 joules is deposited; a thermal insulator 16 of glass is employed having a thickness of 0.1 mm; and a heat-removal element 18 is at an initial temperature of 5.0 degrees Celsius. With reference to FIG. 3, the solid black curve labeled as "−20.0 s" indicates the temperatures of the various elements immediately upon contact of the device to the skin. Twenty seconds later, at time t=0.0 s as shown by the long-dashed curve, note that the epidermis has cooled to approximately 10 degrees Celsius. At this time a current pulse is passed through the heating element 14, causing sheet 12 (in contact with the skin) to rise to nearly 100 degrees C., and the layer of skin within 100 microns of the surface (approximately the location of the epidermis 10) rises to a temperature of 50 to approximately 95 degrees C. (as shown by the short-dashed curve) resulting in the desired cell damage. After 100 milliseconds (at the completion of energy deposition into the heating element) sheet 12 begins to cool. This can be seen by reference to the solid gray curve in FIG. 3, which is calculated at a time of t=0.2 s, or 100 milliseconds after the heating element is turned off. The simulation shows that the epidermis 10 reaches an average temperature of about 70 degrees Celsius, but only for the very brief period of about 100 milliseconds, before heat transfer both into the dermis 11 and heat-removal element 18 return the epidermis to near normal temperature. The remaining curves of dots and crosses indicate the thermal profiles at 0.5 s and 15 s, respectively, after the activation of the heating element 14. Thus the computer model verifies that the desired thermal damage to the epidermis can be effected in a handheld device that, in its most desired embodiment, is both battery-powered and both simple and safe enough for home use.

Alternative Embodiments

The utility of the apparatus and method disclosed above is not limited to the treatment of benign pigmented lesions. For example, it is known that new collagen can be generated by thermal stimulation of the skin, reducing the appearance of facial wrinkles. Similarly, the appearance of a person suffering from acne may be improved by the application of the thermal pulse produced by the subject invention, through destruction of bacteria or unclogging of facial pores. Thus the present invention may be well suited for these dermatologic conditions as well, particularly for home treatment.

While exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention, as set forth in the appended claims and structural and functional equivalents thereof.

In addition, in methods that may be performed according to preferred embodiments herein and that may have been described above, the operations have been described in selected typographical sequences. However, the sequences have been selected and so ordered for typographical convenience and are not intended to imply any particular order for performing the operations, unless expressly set forth in the claims or as understood by those skilled in the art as being necessary.

We claim:

1. Apparatus for treatment of a dermatological condition on a region of human skin by causing a thermal injury to the skin, comprising:
   an energy source,
   a surface of the apparatus configured for contact with the region of skin and capable of being rapidly heated and cooled,
   an ohmic heating element within the apparatus and thermally coupled to the surface,
   a heat removal element within the apparatus and thermally coupled to the surface, and
   electronic control circuitry for generating a thermal pulse in the ohmic heating element to cause rapid heating of the surface sufficient to cause thermal injury to the skin and thereafter to permit rapid cooling of the surface, the thermal pulse having a rate of heating, maximum temperature, and rate of cooling configured to confine the thermal injury primarily to the skin, wherein the energy source is coupled to the ohmic heating element for a selected period of time, and wherein the heat removal element includes a thermal insulating portion and a heat absorbing portion, wherein the thermal insulating portion is configured to have a thermal transfer rate so that it operates as a thermal insulator during at least a portion of the selected period of time, and as a thermal conductor following the selected period of time.

2. The apparatus of claim 1, further including one or more switches for actuating the electronic control circuitry.

3. The apparatus of claim 2, wherein the electronic control circuitry couples the energy source to the ohmic heating element so that the rapid heating heats the skin to a temperature of at least 60 degrees Celsius in less than 200 milliseconds, and the subsequent rapid cooling cools the skin to a temperature of less than 50 degrees Celsius in less than 500 milliseconds.

4. The apparatus of claim 3, wherein the one or more switches is a contact sensor.

5. The apparatus of claim 3, wherein the surface is cooled below an average temperature of the skin and adapted to be placed in contact with the skin prior to activation of the ohmic heating element.

6. The apparatus of claim 5, wherein the one or more switches includes a contact sensor.

7. The apparatus of claim 2, wherein the one or more switches includes a contact sensor.

8. The apparatus of claim 2, wherein the surface is cooled below an average temperature of the skin and adapted to be placed in contact with the skin prior to activation of the ohmic heating element.

9. The apparatus of claim 8, wherein the one or more switches is a contact sensor.

10. The apparatus of claim 1, wherein the thermal insulating portion is a layer selected from a group of materials including transparent tape, glass or mica, and the heat absorbing portion is selected from a block of metal, a phase change material, a thermo-electric module, or a finned heatsink.

11. The apparatus of claim 1 wherein the energy source provides direct current.

12. Apparatus for treatment of a lesion on a region of skin, comprising:
an energy source for providing electrical energy,
a surface of the apparatus configured for contact with the lesion and capable of being rapidly heated and cooled,
an ohmic heating element within the apparatus and thermally coupled to the surface,
a heat removal element within the apparatus and thermally coupled to the surface, wherein the surface is capable of being heated more rapidly than the heat removal element,
electronic control circuitry, responsive to an activation signal, which couples the energy source to the ohmic heating element for generating a thermal pulse at the surface by causing rapid heating of the surface sufficient to cause thermal injury to the skin and thereafter permitting rapid cooling of the surface, the thermal pulse having a rate of heating, maximum temperature, duration and rate of cooling configured to confine thermal injury primarily to the region of skin,
wherein the energy source is coupled to the ohmic heating element for a selected period of time, and
wherein the heat removal element includes a thermal insulating portion and a heat absorbing portion, wherein the thermal insulating portion is configured to have a thermal transfer rate so that it operates as a thermal insulator during at least a portion of the selected period of time, and as a thermal conductor following the selected period of time.

13. The apparatus of claim 12, further including one or more switches and wherein the activation signal is provided by the one or more switches.

14. The apparatus of claim 13, wherein the one or more switches includes a contact sensor.

15. The apparatus of claim 13, wherein the surface is cooled below an average temperature of the skin and adapted to be placed in contact with the skin prior to activation of the ohmic heating element.

16. The apparatus of claim 15, wherein the one or more switches is a contact sensor.

17. The apparatus of claim 13, wherein the power level or duration, or both, are selected so that the rapid heating heats the lesion to a temperature of at least 60 degrees Celsius in less than 200 milliseconds, and the subsequent rapid cooling cools the lesion to a temperature of less than 50 degrees Celsius in less than 500 milliseconds.

18. The apparatus of claim 17, wherein the one or more switches is a contact sensor.

19. The apparatus of claim 17, wherein the surface is cooled below an average temperature of the skin and adapted to be placed in contact with the skin prior to activation of the ohmic heating element.

20. The apparatus of claim 19, wherein the one or more switches includes a contact sensor.

21. The apparatus of claim 12 wherein the energy source provides direct current.

22. An apparatus for treatment of a lesion on a region of skin, comprising:
an energy source for providing electrical energy,
a skin-contacting surface of the apparatus configured for contact with the lesion and capable of being rapidly heated,
a heating element region including an ohmic heating element within the apparatus and thermally coupled to the skin-contacting surface,
electronic control circuitry which couples the energy source to the ohmic heating element for generating a thermal pulse at the surface sufficient to cause thermal injury to the skin by causing rapid heating of the skin-contacting surface, the thermal pulse having a rate of heating, maximum temperature, and duration configured to confine the thermal injury primarily to the region of skin containing the lesion,
a cooled heat removal element for cooling the skin, and
a thermal insulating layer disposed between the cooled heat removal element and the ohmic heating element,
wherein the thermal insulating layer is configured with a thermal transfer rate such that (a) during the thermal pulse, the thermal insulating layer operates as a thermal insulator to insulate the cooled heat removal element from the heated ohmic heating element, and (b) at least one of before and after the thermal pulse, the thermal insulating layer operates as a thermal conductor such that the cooled heat removal element is thermally coupled to the skin-contacting surface via at least the heating element region and the thermal insulating layer, in order to cool the skin at least one of before and after the thermal pulse.

23. The apparatus of claim 22 wherein the electronic control circuitry couples the energy source to the ohmic heating element so that the rapid heating heats the skin to a temperature of at least 60 degrees Celsius in less than 200 milliseconds.

24. The apparatus of claim 22, wherein the surface is cooled below an average temperature of the skin and adapted to be placed in contact with the skin prior to activation of the ohmic heating element.

25. The apparatus of claim 22 wherein the thermal injury is confined primarily to the epidermal region of the skin.

26. The apparatus of claim 22 wherein the energy source provides direct current.

27. An apparatus for treatment of a region of skin, comprising:
- an energy source for providing electrical energy,
- a skin-contacting surface of the apparatus configured for contact with the skin and capable of being rapidly heated,
- a heating element region including an ohmic heating element thermally coupled to the apparatus surface, and
- electronic control circuitry which couples the energy source to the ohmic heating element to cause rapid heating of the skin-contacting surface sufficient to cause thermal injury to the skin, the thermal pulse having a rate of heating, maximum temperature, and duration configured to control the thermal injury of the skin,
- wherein all or substantially all of the heating of the skin by the apparatus is caused by thermal heat transfer from the ohmic heating element, through the skin-contacting surface, and to the skin,
- a cooling element for cooling the skin, and
- a thermal insulating layer disposed between the cooling element and the ohmic heating element,
- wherein the thermal insulating layer is configured with a thermal transfer rate such that (a) during the thermal pulse, the thermal insulating layer operates as a thermal insulator to insulate the cooling element from the heated ohmic heating element, and (b) at least one of before and after the thermal pulse, the thermal insulating layer operates as a thermal conductor such that the cooling element is thermally coupled to the skin-contacting surface via at least the heating element region and the thermal insulating layer, in order to cool the skin at least one of before and after the thermal pulse.

28. Apparatus for treatment of a region of skin by thermal heating, comprising:
- an energy source for providing electrical energy,
- one and only one energy-transferring contact configured to facilitate energy transfer between the apparatus and the skin,
- an ohmic heating element within the apparatus and thermally coupled to the single energy-transferring contact,
- a heat removal element within the apparatus and thermally coupled to the single energy-transferring contact, and
- electronic control circuitry which couples the energy source to the ohmic heating element for rapidly heating the single energy-transferring contact to generate a thermal pulse for delivery to the skin, the thermal pulse having a rate of heating, maximum temperature, and duration configured to control the thermal injury of the skin,
- a cooling element for cooling the skin,
- wherein the heating element region is positioned between the cooling element and the energy-transferring contact, such that the cooling element is thermally coupled to the energy-transferring contact through at least the heating element region;
- such that the one and only one energy-transferring contact is used for both (a) heating the skin during the thermal pulse, via the thermal coupling of the ohmic heating element with the energy-transferring contact, and (b) cooling the skin at least one of before and after the thermal pulse, via the thermal coupling of the cooling element with the energy-transferring contact.

* * * * *